United States Patent
Joshi et al.

(10) Patent No.: US 8,824,756 B2
(45) Date of Patent: Sep. 2, 2014

(54) IMAGE RECONSTRUCTION INCORPORATING ORGAN MOTION

(75) Inventors: Sarang Joshi, Salt Lake City, UT (US);
Jacob Hinkle, Salt Lake City, UT (US);
Bill Salter, Salt Lake City, UT (US);
Tom Fletcher, Salt Lake City, UT (US);
Brian Wang, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 140 days.

(21) Appl. No.: 13/381,206

(22) PCT Filed: Jun. 30, 2010

(86) PCT No.: PCT/US2010/040582
§ 371 (c)(1),
(2), (4) Date: Apr. 26, 2012

(87) PCT Pub. No.: WO2011/002874
PCT Pub. Date: Jan. 6, 2011

(65) Prior Publication Data
US 2012/0201428 A1   Aug. 9, 2012

Related U.S. Application Data

(60) Provisional application No. 61/222,028, filed on Jun. 30, 2009.

(51) Int. Cl.
*G06K 9/00* (2006.01)
*G06T 11/00* (2006.01)
*A61B 6/00* (2006.01)
*G06F 17/30* (2006.01)
*A61B 8/00* (2006.01)
*A61B 5/00* (2006.01)

(52) U.S. Cl.
CPC .......... *G06T 11/006* (2013.01); *G06K 9/00442* (2013.01); *A61B 6/5247* (2013.01); *G06F 17/30247* (2013.01); *A60B 6/00* (2013.01); *G06T 2211/412* (2013.01); *A61B 8/00* (2013.01); *A61B 5/7289* (2013.01)
USPC .......................................................... 382/128

(58) Field of Classification Search
USPC ....................................... 382/107, 131; 378/8
See application file for complete search history.

(56) References Cited

U.S. PATENT DOCUMENTS 6,894,494 B2   5/2005   Stergiopoulos et al.
7,221,728 B2   5/2007   Edic et al.

(Continued)

OTHER PUBLICATIONS

International Search Report and Written Opinion issued for PCT/US2010/040582, dated Sep. 1, 2010, 9 pages.

*Primary Examiner* — Hadi Akhavannik
(74) *Attorney, Agent, or Firm* — Michael Best & Friedrich LLP

(57) ABSTRACT

Systems and methods which implement an image reconstruction framework to incorporate complex motion of structure, such as complex deformation of an object or objects being imaged, in image reconstruction techniques are shown. For example, techniques are provided for tracking organ motion which uses raw time-stamped data provided by any of a number of imaging modalities and simultaneously reconstructs images and estimates deformations in anatomy. Operation according to embodiments reduces artifacts, increase the signal-to-noise ratio (SNR), and facilitates reduced image modality energy dosing to patients. The technology also facilitates the incorporation of physical properties of organ motion, such as the conservation of local tissue volume. This approach is accurate and robust against noise and irregular breathing for tracking organ motion.

31 Claims, 11 Drawing Sheets

(56) References Cited

U.S. PATENT DOCUMENTS

| | | | |
|---|---|---|---|
| 2002/0025017 A1* | 2/2002 | Stergiopoulos et al. | 378/8 |
| 2003/0099391 A1* | 5/2003 | Bansal et al. | 382/131 |
| 2005/0113671 A1* | 5/2005 | Salla et al. | 600/413 |
| 2006/0133564 A1* | 6/2006 | Langan et al. | 378/8 |
| 2006/0140482 A1 | 6/2006 | Koehler | |
| 2007/0183639 A1* | 8/2007 | Kohler et al. | 382/131 |
| 2008/0095422 A1* | 4/2008 | Suri et al. | 382/131 |
| 2008/0292163 A1* | 11/2008 | DiBella et al. | 382/131 |

\* cited by examiner

IMAGE RECONSTRUCTION INCORPORATING ORGAN MOTION

CROSS-REFERENCE TO RELATED APPLICATIONS

This application claims priority to U.S. Provisional Patent Application No. 61/222,028 entitled "IMAGE RECONSTRUCTION INCORPORATING ORGAN MOTION," filed Jun. 30, 2009, the disclosure of which is hereby incorporated herein by reference.

TECHNICAL FIELD

The disclosure relates generally to imaging and, more particularly, to reconstructing images which incorporate motion.

BACKGROUND OF THE INVENTION

Imaging techniques have been developed for studying organs where motion is present. For example, four-dimensional respiratory-correlated computed tomography (4D RCCT) has been widely used for studying organs where motion is associated with patient breathing. The current standard practice for reconstructing images with respect to such organ motion is to use phase binned images. However, the phase binning algorithm assumes that the patient has a periodic breathing pattern. When the patient's breathing is irregular as represented in the graph of FIG. 1A, this assumption breaks down and significant image artifacts like that indicated by the arrow of FIG. 1B are introduced.

A recent extensive study found that 90% of 4D RCCT patient images had at least one artifact. Amplitude binning algorithms have been developed as a way to alleviate these artifacts by assuming that the underlying anatomical configuration is correlated to the amplitude of the breathing signal.

For example, during a typical 4D RCCT fan-beam scan, the patient passes through the scanner on an automated couch that pauses at regular intervals to collect data. At each couch position slices are acquired repeatedly (e.g., 15-20 times). Each slice is acquired by collecting a series of projections at different angles. The slices are then reconstructed individually using filtered back-projection. The speed of acquisition of each slice is dependent on the scanner and for current generation multi-slice scanners is generally on the order of 0.5 s. The X-ray detection process used to acquire slices is subject to Poisson noise. However, at the X-ray tube currents typically used in clinical practice the signal is strong enough that the noise is approximately Gaussian. The patient's breathing is monitored during acquisition using an external surrogate for internal organ motion. The resulting breathing trace, a(t), is used to tag the acquired projection retrospectively with a breathing amplitude. An example of a breathing trace monitoring system is the Real-time Position Management (RPM) system (Varian Oncology Systems, Palo Alto, Calif.), which uses a camera to track infrared-reflective markers attached to the patient's torso.

Although application of amplitude binning algorithms in the foregoing example may reduce binning artifacts, since data is not acquired at all breathing amplitudes the images often have some missing slices. Accordingly, image artifacts continue to be present in the reconstructed images.

Modeled rigid 2D motion has been used during image acquisition to alleviate in-plane artifacts in fan-beam CT. However, such rigid 2D motion models are not valid for imaging of the torso, where respiratory-induced motion causes highly non-linear deformation with a significant component in the superior-inferior direction.

Another prior method reconstructs a full 4D time-indexed image using a B-spline motion model and a temporal smoothing condition. Yet other B-spline-based methods require an artifact-free reference image (such as a breath-hold image) in addition to a 4D fan-beam or cone-beam scan. These approaches address difficulties caused by slowly-rotating cone-beam scanners. However, the acquisition of an artifact-free reference image remains impractical for many radiotherapy patients. While the B-spline model guarantees smooth deformations, it cannot guarantee the diffeomorphic properties for large deformations and it does not directly enforce local conservation of tissue volume.

In another previous method, 3D images are reconstructed at arbitrary amplitudes by interpolating each slice from those collected at nearby amplitudes and then stacking them. Two slices are used to interpolate a slice at the desired amplitude using an optical flow algorithm, so only 2D motion can be estimated. A more recent approach has used a 4D cone-beam scan to estimate organ motion using an optical flow approach. The motion estimate is then used to correct for organ motion during subsequent 3D scans on the fly. This method may be useful in reducing artifacts in a 3D image, but the optical flow model, like the B-spline model, does not ensure diffeomorphic incompressible motion estimates.

As early as 1991, an incompressible optical flow method for image registration was used. Some systems have used a spline-based model which penalizes tissue compression to perform incompressible image registration. Other researches have studied incompressible fluid-based registration of liver computed tomography (CT). An incompressible fluid-based approach solves Poisson's equation via a multigrid method at each iteration. Another efficient Fourier method of incompressible projection applies a result from the continuous domain to discrete data without alteration, which does not accommodate the discrete nature of image data. Despite these efforts in image registration, the incompressible nature of internal organs has not previously been incorporated into the image reconstruction process.

Deformable image registration has been shown to be useful in tracking organ motion in artifact-free 4D RCCT images. Such methods may be used with either phase or amplitude binned images, but are challenged in the presence of binning artifacts. That is, deformable image registration is not well suited for use with respect to 4D RCCT images which include binning artifacts.

From the above, it can be appreciated that regeneration of images where motion is present is problematic. In particular, motion artifacts remain present despite application of many of the available image reconstruction techniques. Moreover, none of the present imaging reconstruction techniques guarantee the diffeomorphic properties for large deformations or directly enforce local conservation of object volume.

BRIEF SUMMARY OF THE INVENTION

The present invention is directed to systems and methods which implement an image reconstruction framework to incorporate complex motion of structure, such as complex deformation of an object or objects being imaged, in image reconstruction techniques. Embodiments of image reconstruction frameworks herein are operable with respect to a plurality of image modalities, such as CT, magnetic resonance (MR), positron emission tomography (PET), ultrasound, etc. An image reconstruction framework according to embodiments of the invention utilizes information regarding the nature of motion, information regarding motion tracking, and imaging modality raw image information to jointly provide motion estimation and image reconstruction.

According to embodiments of the invention, systems and methods are provided for reconstructing anatomical images, including one or more organs or other structure (referred to herein generally as objects), of a patient who is being medically imaged. The method may include the operation of collecting raw image data from a medical imaging device configured to obtain anatomical images of a patient's internal anatomy. Motion tracking data can be obtained, wherein such motion tracking data can be related to organ motion as the anatomical images are obtained. In an exemplary embodiment, the motion tracking data may represent breathing motion as measured by a motion sensor with the patient. Additionally or alternatively, the motion tracking data may be measured from raw image data acquired from the medical imaging device.

Continuing with the foregoing example, further operation according to embodiments comprises modeling organ deformation motion using the motion tracking data with correlated raw image data and data regarding the nature of motion of the organ (e.g., motion bounding data for the organ). For example, when modeling organ deformation motion, motion tracking data can be used to indicate attributes of organ motion (e.g., motion timing) in order to facilitate modeling of a patient's internal organs and to obtain organ deformations by an estimation of anatomical deformation during image reconstruction. In one embodiment, modeling of the organ deformations includes using data regarding the nature of motion of the organ to enforce conservation of local tissue volume during organ modeling. Further, data regarding the nature of motion of the organ may provide a diffeomorphic motion model of organ deformations for deformation motion modeling according to embodiments herein.

The organ deformation motion can be used in reconstructing anatomical images. For example, an estimated time-indexed 4D image can then be generated using the organ deformation motion, wherein the estimated time-indexed image is viewable by an end user. The organ deformation motion estimation provided according to embodiments of the present invention can thus be used to reduce motion artifacts and/or increase the signal-to-noise ratio in images being reconstructed. Increased signal-to-noise ratio resulting from implementation of organ deformation motion estimation of embodiments facilitates a decrease in the dose of image modality energy (e.g., X-ray energy, magnetic field energy, ultrasound energy, etc.) delivered to the patient for generating an image of desired quality.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1A:
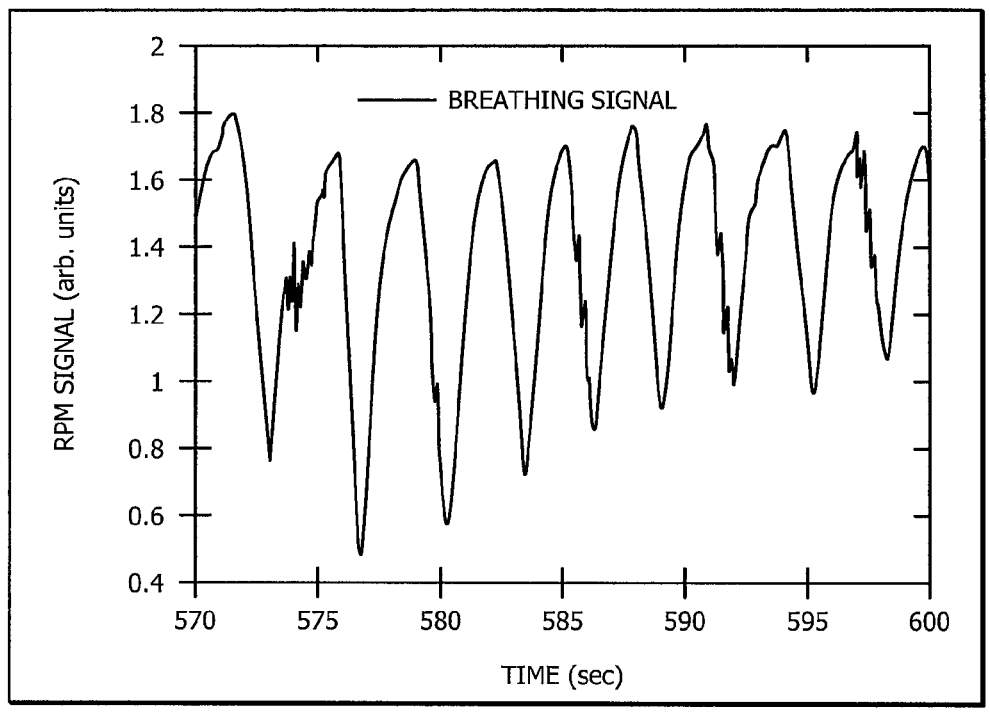
FIG. 1A shows a graph of irregular breathing cycles of a patient for which imaging is provided.
Figure 1B:
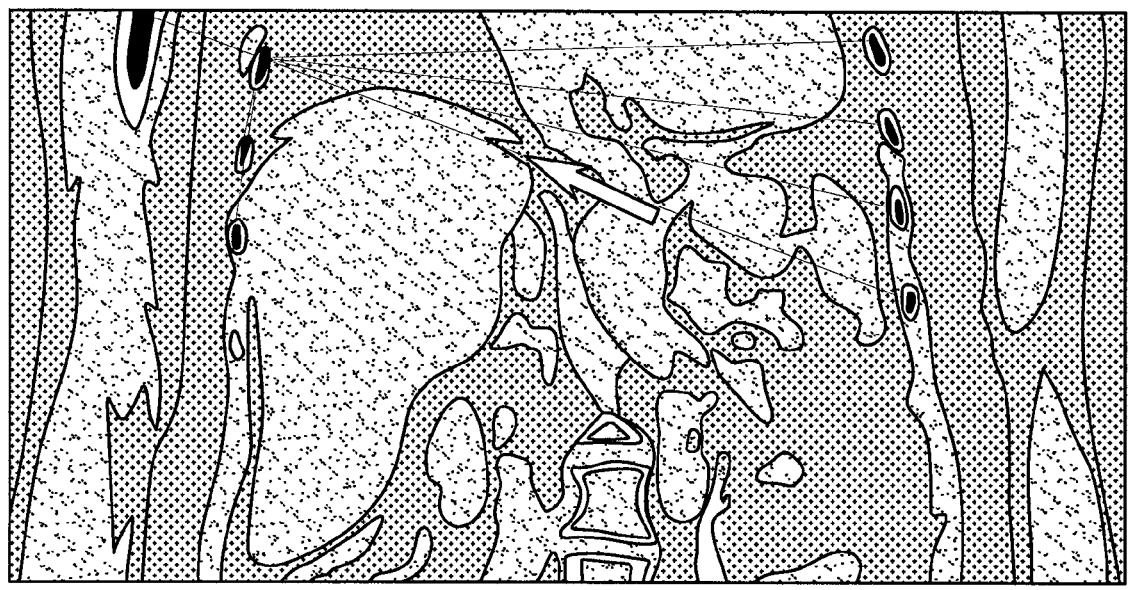
FIG. 1B show an image reconstructed using a phase binning algorithm for image data collected during the irregular breathing cycles of FIG. 1A.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
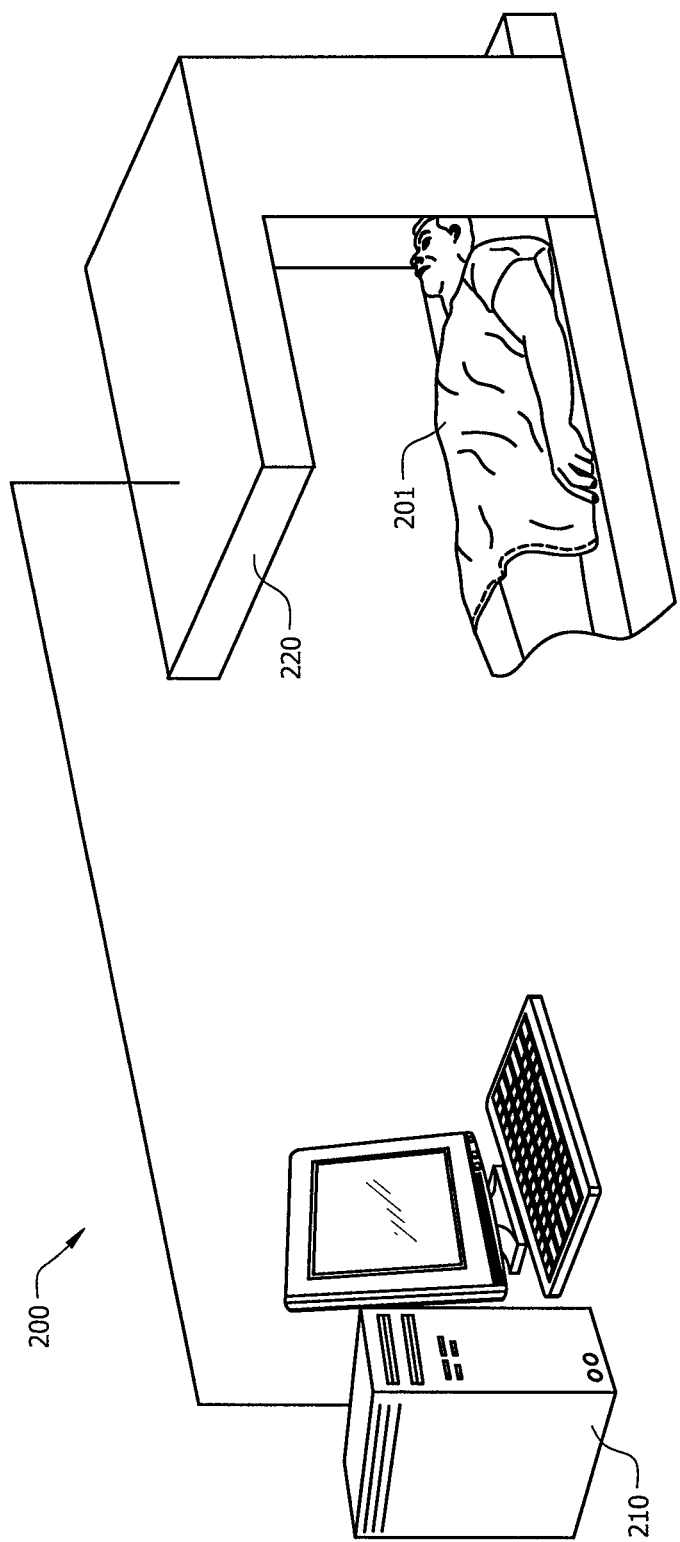
FIG. 2 shows an imaging system adapted according to an embodiment of the present invention.

Directing attention to FIG. 2, an imaging system adapted according to an embodiment of the present invention is shown as imaging system 200. Imaging system 200 comprises processor based system 210 operatively coupled to transducer 220 for use in collecting imaging data with respect to subject 201. For example, subject 201 may comprise a patient for which imaging of a portion of the patient's body (e.g., head, torso, leg, shoulder, etc.) is desired. Such imaging as provided by imaging system 200 may comprise reconstruction of images of internal body structure (e.g., organs, cavities, bones, etc.) using one or more imaging modality (e.g., CT, MR, PET, ultrasound, etc.).

Processor based system 210 of embodiments comprises a processor (e.g., central processing unit (CPU), application specific integrated circuit (ASIC), etc.), memory (e.g., random access memory (RAM), read only memory (ROM), disk memory, optical memory, etc.), and appropriate input/output (I/O) apparatus (e.g., display, pointing device, keyboard, printer, speaker, microphone, etc.) operable under control of an instruction set (e.g., software, firmware, etc.) defining operation as described herein. Such operation may provide image reconstruction using one or more imaging modality corresponding to the configuration of transducer 220. For example, where a CT imaging modality is utilized transducer 220 may comprise an X-ray source and detector configuration, where a MR imaging modality is utilized transducer 220 may comprise a magnetic field generator and receiver configuration, where a PET imaging modality is utilized transducer 220 may comprise a gamma ray source and detector configuration, and where an ultrasound imaging modality is utilized transducer 220 may comprise an ultrasonic sound source and receiver configuration.

Figure 3:
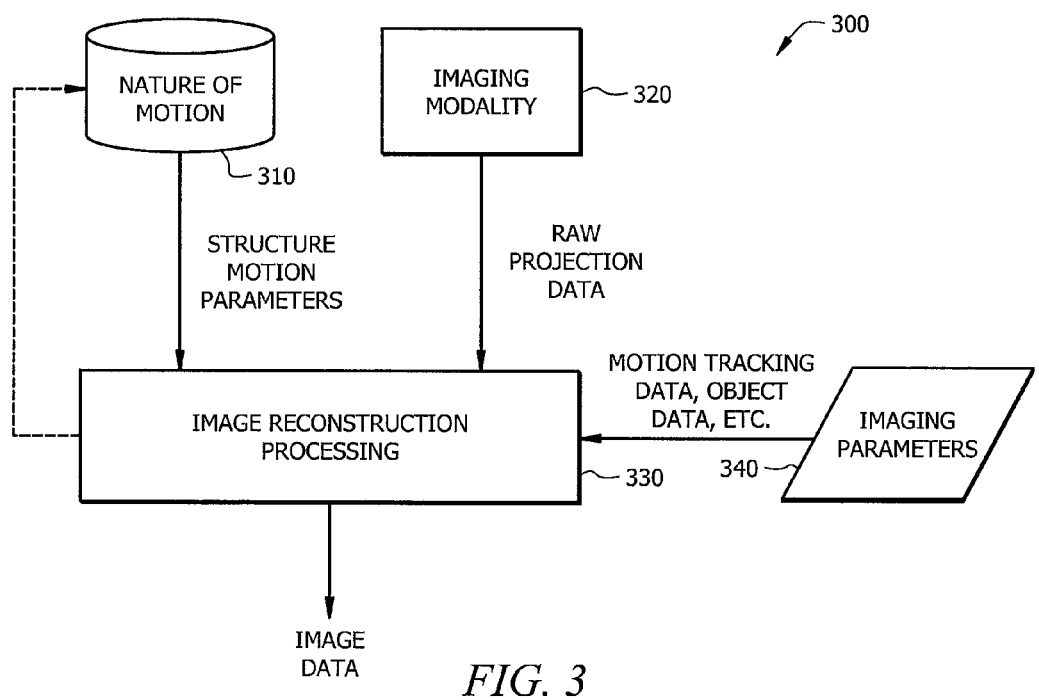
FIG. 3 shows an image reconstruction framework of an embodiment of the present invention as may be utilized in the imaging system of FIG. 2.

Imaging system 200 of embodiments herein is adapted to utilize an image reconstruction framework to incorporate motion of structure, such as complex deformation of an object or objects being imaged, in an image reconstruction technique implemented thereby. An image reconstruction framework as may be utilized by imaging system 200 is shown in FIG. 3 as image reconstruction framework 300. Image reconstruction framework 300 may be implemented, at least in part, as instructions operable upon the processor of processor based system 210 of imaging system 200.

According to embodiments of the invention, image reconstruction framework 300 utilizes information regarding the nature of motion, information regarding motion tracking, and imaging modality raw image information to jointly provide motion estimation and image reconstruction. Accordingly, image reconstruction framework 300 of the illustrated embodiment includes nature of motion database 310 storing information regarding the nature of motion and image reconstruction processing 330 providing image reconstruction processing as described herein. Motion tracking data, structure/object data, and/or other imaging parameters useful in image reconstruction processing according to embodiments is provided to image reconstruction processing 330 by imaging parameter input 340. Additionally, imaging modality raw image information useful in image reconstruction according to embodiments is provided to image reconstruction processing 330 from imaging modality 320 of processor based system 210.

Image reconstruction framework 300 of the illustrated embodiment may operate with respect to various image modalities, such as CT, magnetic resonance (MR), positron emission tomography (PET), ultrasound, etc., and thus imaging modality 320 may comprise one or more such imaging modality. Such image modalities provide raw image information (e.g., raw image projection data) as is understood in the art. The motion model (e.g., anatomical motion model used with respect to organ movement) does not change from modality to modality according to embodiments, thereby facilitating the utilization of an image reconstruction framework herein with any of a number of imaging modalities. However, algorithms of image reconstruction procession 330 are preferably adapted to reconstruct images from the particular raw image information provided by an imaging modality being used.

As will be more fully appreciated from the discussion which follows, image reconstruction processing 330 of embodiments models structure motion jointly with the image at the time of image reconstruction. Operation of image reconstruction processing 330 preferably accommodates complex deformation of structure, as opposed to rigid motion of structure. For example, image reconstruction processing 330 may model the complex deformation that the anatomy undergoes when the subject (e.g., patient) is breathing, the subject's heart is beating, the subject's gastro intestinal track is contracting, etc. Such deformation may comprise incompressible organ deformation (e.g., movement of the liver associated with breathing), compressible organ deformation (e.g., movement of the heart associated with its beating), etc. Thus, the image reconstruction framework of embodiments includes a deformation model which models the entire non-linear movement process and builds a movement estimation utilized in image reconstruction.

In facilitating modeling such a non-linear movement process, nature of motion database 310 comprises structure motion parameters (e.g., object motion bounding data) for use in modeling one or more objects. For example, structure motion parameters may comprise information regarding constraints on possible deformations of a medium, particular structure or a particular object, etc. (e.g., limits on or bounds on movement that may be experienced by an object). Such structure motion parameters may comprise boundaries (e.g., upper and/or lower limits) regarding velocity, changes in velocity, etc. for a medium, particular structure, etc. Structure motion parameters may be derived or estimated using mathematical analysis techniques such as b-spline, polynomial-spline, elastic-spline, ploy-affine, polynomial, wavelet based, and/or the like. It can be appreciated that different media, structure, objects, etc., may have different properties associated therewith (e.g., density, rigidity, fluidity, etc.) which affect the movement (e.g., deformation) thereof. By utilizing appropriate structure motion parameters, as may be provided by nature of motion database 310, embodiments of image reconstruction processing 330 may effectively estimate movement of structure within an image being reconstructed. That is, although an exact model of the movement of structure may not be known, limits on how such movement occurs (e.g., how fast, how smooth, etc.) may be known from which structure movement may be estimated herein.

In embodiments of image reconstruction processing 330, a maximum a posteriori (MAP) method is provided for tracking structure motion that uses raw time-stamped image information to reconstruct the images and estimate structure deformations simultaneously. Accordingly, the raw image information (e.g., raw projection data) provided by imaging modality 320 is preferably time-stamped or otherwise adapted for indexing with motion tracking data. For example, time-stamp indexing of raw projection data may be utilized with respect to motion tracking data (e.g., provided by imaging parameter input 340) related to structure motion as the raw image projections are obtained (e.g., organ motion as the subject is being imaged). Having indexed the raw projection data to the motion tracking data, operation of image reconstruction processing 330 of embodiments estimates motion of structure within the image using the aforementioned structure motion parameters. The particular structure motion parameters utilized with respect to structure, an object, an image, etc. may be selected based upon structure data (e.g., provided by imaging parameter input 340). For example, particular structure being imaged, a particular object being imaged, a particular region of the anatomy, a particular media, a particular characteristic (e.g., rigid, fluid filled, gaseous, etc.) may be identified by the structure data for selection of one or more appropriate structure motion parameters. It should be appreciated that the imaging parameters provided by imaging parameter input 340 may be provided by user input, collected by one or more sensor, may be derived from other data, and/or the like.

Neither the desired image nor the exact motion of the structure in the image are known at initiation of operation of image reconstruction processing 330 of embodiments. Nevertheless, image reconstruction processing 330 of embodiments implements an alternating optimization algorithm to find the solution to both of these problems at the same time, using the aforementioned information regarding the nature of motion. For example, using equations derived from Navier-Stokes equations embodiments of image reconstruction processing 330 are able to provide mechanical modeling of tissue which accommodates various different tissue properties from rigid, uncompressible to very compressible, soft tissue motion. It should be appreciated that the global structure of the equations may be determined a priori and preferably the parameters utilized in solving the aforementioned problems may be optimized during operation of the estimation algorithm (as represented by feedback shown by the dotted line of FIG. 3).

The method eliminates artifacts as it does not rely on a binning process and increases signal-to-noise ratio (SNR) by using all of the collected data. In the case of CT, the increased SNR provides the opportunity to reduce dose to the patient during scanning. This technology also facilitates the incorporation of fundamental physical properties such as the conservation of local tissue volume during the estimation of the organ motion. This method is accurate and robust against noise and irregular breathing for tracking organ motion and reducing artifacts. An improvement in image quality is also demonstrated by application of the method to data from a real liver stereotactic body radiation therapy patient.

As can be appreciated from the foregoing, previous attempts at reducing 4D RCCT motion artifacts do not offer all the advantages of the described method, which incorporates a fully diffeomorphic motion model into the reconstruction process. For instance, rigid 2D motion models are not valid for imaging of the torso, where respiratory-induced motion causes highly non-linear deformation with a significant component in the superior-inferior direction. B-spline-based methods require an artifact-free reference image (such as a breath-hold image) in addition to a 4D fan-beam or cone-beam scan. However, the acquisition of an artifact-free reference image is impractical for many radiotherapy patients. Moreover, while the B-spline model guarantees smooth deformations, it cannot guarantee the diffeomorphic properties for large deformations ensured by the method described herein and it does not directly enforce local conservation of tissue volume. A 4D cone-beam scan used to estimate organ motion using an optical flow approach may be useful in reducing artifacts in a 3D image, but the optical flow model, like the B-Spline model, does not ensure diffeomorphic incompressible motion estimates.

Having described the concepts of the invention broadly, exemplary embodiments will be provided below which provide detail helpful in understanding the concepts herein. The exemplary embodiments presented below are general examples as may be implemented using imaging system 200 of FIG. 2 and image reconstruction framework 300 of FIG. 3. It should be appreciated that the particular exemplary embodiments, and their associated detail, are intended to facilitate an understanding of the concepts of the present invention and do not present limitations regarding various embodiments thereof. For example, although the exemplary embodiments presented herein are discussed with respect to application to signals recorded by breathing monitoring systems, such as spirometry or chest circumference tracking, other motion tracking systems may be utilized. Likewise, although discussed below with respect to application to 4D RCCT of the liver, the methods may be applied to other organ motion, such as cardiac motion using the ECG signal in place of a breathing monitor.

The 4D image reconstruction of embodiments estimates the time-indexed image I(t, x) that best represents the patient's anatomy during image acquisition. In order to obtain a maximum a posteriori estimate of organ motion the data likelihood is derived and a prior model incorporating the physical constraints is preferably defined. The 4D image that maximizes the posterior probability combining the data likelihood and the prior is estimated according to embodiments.

CT image acquisition, as may be utilized according to embodiments of the invention, is described by a projection operator, $P_\theta$, which can represent fan-beam or cone-beam projections at angle $\theta$. At sufficiently high signal-to-noise ratio, the acquisition of a single projection $p_i$ is subject to Gaussian noise of variance $\sigma^2$. The data log-likelihood then becomes $$L(\{p_i\} \mid I(t, x)) = -\frac{1}{2\sigma^2} \sum_i \int_S |P_{\theta_i}\{I(t_i, x)\}(s) - p_i(s)|^2 ds, \quad (1)$$

where the integration with respect to s is over a one or two-dimensional domain depending on the projection operator used.

Due to the sparsity of the imaging data, it is desirable to constrain the estimation. Specifically, it can be assumed that no metabolic changes or local tissue density variations occur during acquisition and that the only dynamic process is the motion of the anatomy due to breathing. Under this assumption, the 4D image is described by a time-indexed deformation field and a single representative static 3D image, $I_0(x)$, as $$I(t,x)=I_0(h(t,x)), \quad (2)$$

where for each time t, h(t, .) is a volume-preserving diffeomorphic deformation capturing the respiratory-induced motion of the underlying anatomy.

The organ motion may be assumed to be correlated with breathing amplitude, so the deformation may be indexed by amplitude alone. Under this assumption, the deformations take the form h(a(t), x). The velocity of a point in the patient's anatomy is then described by the ordinary differential equation $$\frac{d}{dt}h(a(t), x) = v(a(t), h(a(t), x))\frac{da}{dt}, \quad (3)$$

where v is indexed by amplitude and may be thought of as a velocity with respect to changes in amplitude rather than time. The deformation from zero amplitude to any other amplitude is given by the associated integral equation $$h(a,x)=x+\int_0^a v(a',h(a',x))da'. \quad (4)$$

If the velocities are constrained to be smooth, the resulting estimates of patient anatomy are at all times diffeomorphic to one another. This ensures that organs do not tear or disappear during breathing. The diffeomorphic deformations provide a one-to-one correspondence between points in images from different breathing amplitudes, enabling tracking of tissue trajectories. Smoothness is enforced according to embodiments by introducing a prior on the velocities via a Sobolev norm $\|\upsilon\|_V^2$, defined by $$\|\upsilon\|_V^2 = \langle \upsilon, \upsilon \rangle_V = \int_0^1 \int_{x \in \Omega} \|L\upsilon(a,x)\|_{R^3}^2 dx da \quad (5)$$

where L is a differential operator chosen to reflect physical tissue properties. In addition, the homogeneous operator, L can be spatially-varying reflecting the different material properties of the underlying anatomy.

Deformations defined by the flow along smoothly-varying vector fields as described in equation 3 have been well studied. In particular, if the divergence of the velocity field is zero the resulting deformation is guaranteed to preserve volume locally and have unit Jacobian determinant. This is a necessary constraint when modeling the breathing induced motion of incompressible fluid-filled organs such as liver. In fact, if L is the Laplacian operator and the velocities are constrained to be divergence-free, the velocities simulate Stokes flow of an incompressible viscous fluid.

With the data log-likelihood and the prior model described above, the log-posterior probability of observing the data becomes $$L(I_0, \upsilon \mid p_i) = \quad (6)$$
$$-\|\upsilon(a)\|_V^2 - \frac{1}{2\sigma^2} \sum_i \int_S |P_{\theta_i}\{I_0 \circ h(a_i, x, y, z_i)\}(s) - p_i(s)|^2 ds,$$

subject to $div\ \upsilon = 0$.

Having defined the posterior, the 4D image reconstruction of embodiments can estimate the image and deformations parameterized by the velocity field that maximize equation 6, $$(\hat{I}_0, \hat{\upsilon}) = \underset{I_0, \upsilon}{\mathrm{argmax}} L(I_0, \upsilon \mid P_i) \text{ subject to } div\ \upsilon = 0. \quad (7)$$

A MAP estimate that maximizes equation 6 may be obtained via an alternating iterative method which at each iteration updates the estimate of the deformation in a gradient ascent step then updates the image using the associated Euler-Lagrange equation. The continuous amplitude indexed velocity field may be discretized by a set of equally-spaced amplitudes $a_k$ with the associated velocities $\upsilon_k$, with spacing $\Delta a$. Note that this amplitude discretization is independent of the amplitudes at which data is acquired. The deformation from amplitude $a_k$ to $a_{k+1}$ is approximated according to embodiments by the Euler integration of equation 4, $$h(a_{k+1}, x) = h(a_k, x) + \upsilon_k(h(a_k, x)) \quad (8)$$

and the deformation for an amplitude $a_i$ between $a_k$ and $a_{k+1}$ is linearly interpolated according to embodiments as $$h(a_i, x) = h(a_k, x) + \frac{a_i - a_k}{\Delta a} \upsilon_k(h(a_k, x)) \quad (9)$$

Note that higher order integration schemes, such as Runge-Kutta, may also be used in place of the simpler Euler method, if desired.

A first variation of equation 6 with respect to Vk under the inner product in equation 5 is given by $$\delta_{\upsilon_k} L(I_0, \upsilon_k \mid p_i) = \quad (10)$$
$$-2\upsilon_k - \frac{1}{\sigma^2}(L^\dagger L)^{-1} \sum_i P_{\theta_i}^\dagger (P_{\theta_i}\{I_0 \circ h(a_i, \cdot)\} - p_i) b_i(k, \cdot),$$

where $b_i$ is the contribution to the variation due to a single projection and $P_{\theta_i}^+$ is the adjoint of the projection operator, which acts by back projecting the data discrepancy back into the 3D volume. The adjoint operators for various imaging geometries have been well studied. For parallel-beam CT geometry, the adjoint projection operator is the familiar back-projection operator. Conventional filtered backprojection CT slice reconstruction involves applying the adjoint operator, after filtering the 1D data. Let $I_k(x) = I_0 \circ h(a_k, x)$ be the 3D reference image pushed forward to amplitude $a_k$, the factors $b_i$ are given by $$b_i(k, x) = \begin{cases} 0 & a_i \leq a_k \\ \frac{a_i - a_k}{\Delta a} \nabla I_k\left(x + \frac{a_i - a_k}{\Delta a} \upsilon_k(x)\right) & a_k < a_i \leq a_{k+1} \\ |D(h_{a_{k+1}} \circ h_{a_i}^{-1})(x)| \nabla I_k(x + \upsilon_k(x)) & a_i > a_{k+1} \end{cases} \quad (11)$$

If the deformations are constrained to be incompressible, implying that the Jacobian determinant is unity, this simplifies to $$b_i(k, x) = \begin{cases} 0 & a_i \leq a_k \\ \frac{a_i - a_k}{\Delta a} \nabla I_k\left(x + \frac{a_i - a_k}{\Delta a} \upsilon_k(x)\right) & a_k < a_i \leq a_{k+1} \\ \nabla I_k(x + \upsilon_k(x)) & a_i > a_{k+1} \end{cases} \quad (12)$$

An efficient computation of $(L^\dagger L)^{-1}$ may be implemented in the Fourier domain, wherein only a matrix multiplication and Fourier transforms of $\upsilon_k$ at each iteration of the algorithm may be utilized.

The Helmholtz-Hodge decomposition enables the implementation of the incompressibility constraint by simply projecting the unconstrained velocity fields onto the space of divergence free vector fields at each iteration of the method. In order to efficiently implement the Helmholtz-Hodge decomposition of a time-varying velocity field, the discrete divergence operator can be used as the operator operates in Fourier domain. The discrete Fourier transform of a central difference approximation to the derivative of a function $f$ can be written as $$DFT\{\Delta_z f\}(\omega) = DFT\left\{\frac{f(x+k_x) - f(x-k_x)}{2k_x}\right\}(\omega) \quad (13)$$
$$= \frac{i}{2k_x} \sin \omega DFT\{f\}(\omega)$$

In the Fourier domain the divergence of a vector field takes the following form:

$$DFT\{div\ \upsilon\}(\omega) = W(\omega) \cdot DFT\{\upsilon\}(\omega), \quad (14)$$

where $$W(\omega) = \frac{i}{2} \begin{pmatrix} \frac{1}{k_x} \sin\frac{\omega_x}{N_x} \\ \frac{1}{k_y} \sin\frac{\omega_y}{N_y} \\ \frac{1}{k_z} \sin\frac{\omega_z}{N_z} \end{pmatrix} \quad (15)$$

The foregoing allows the divergent component to be easily removed in Fourier space via the projection $$DFT\{v\}(\omega) \to DFT\{v\}(\omega) - \frac{W(\omega) \cdot DFT\{v\}(\omega)}{\|W(\omega)\|\frac{2}{C^3}} W(\omega) \quad (16)$$

Since the operator $(L^{\dagger}L)^{-1}$ is implemented in the Fourier domain according to embodiments there is little computational overhead in performing this projection at each iteration of the image reconstruction algorithm.

A first variation of equation 6 with respect to $I_0$ is $$\delta_{I_0} L(I_0, v \mid p_i) = \quad (17)$$
$$\frac{1}{\sigma^2} \sum_i |Dh^{-1}(a_i, \cdot)|(P^{\dagger}_{\theta_i} P_{\theta_i}\{I_0 \circ h(a_i, \cdot)\} - P^{\dagger}_{\theta_i} p_i) \circ h^{-1}(a_i, \cdot)$$

If organ motion is slow compared to single slice acquisition time, individual slices can be reconstructed with minimal motion artifacts using filtered backprojection. In this case the 4D image is estimated from the reconstructed 2D slices $S_i(x, y)$. Note that this assumption holds reasonably well in the case of 4D RCCT. Under the slow motion assumption, the velocity field variation becomes $$\delta_{v_k} L(I_0, v_k \mid p_i) = -2v_k - \frac{1}{\sigma^2}(L^{\dagger}L)^{-1}\sum_i (I_0 \circ h(a_i, \cdot) - S_i) b_i(k, \cdot) \quad (18)$$

For slice data, $S_i$, and an incompressible deformation estimate equation 17 may be solved by the mean of the deformed data, $$\hat{I}_0(x) = \frac{1}{N} \sum_{i, h^{-1}(a_i; x)_z = z_i} S_i \circ h^{-1}(a_i, x), \quad (19)$$

which is equivalent to solving the Euler-Lagrange equation for equation 6.

Note that as soon as the velocity field is updated, the image estimate should also be updated. The change of image estimate in turn alters the velocity gradients leading to a joint estimation algorithm in which, at each iteration, the velocity fields are updated and then the image is recalculated.

A 4D reconstruction method for slice data according to embodiments of the present invention is set forth in the pseudocode below. In the method of the pseudocode, the velocity fields are initialized to zero, so that the initial estimate of the base image is simply the result of averaging all of the data. This yields a quite blurry image that sharpens upon further iterations as the motion estimate improves.

---

Pseudocode for 4D reconstruction of of slice data
   $I_0 \leftarrow 0$
   for each k do
      $v_k \leftarrow 0$
   end for
   repeat $$I_0 \leftarrow \frac{1}{N}\sum S_i \circ h^{-1}(a_i, x)$$

for each k do
         $v_k \leftarrow v_k + \epsilon \delta_{v_k} L(I_0, v_k)$
      end for
      Perform divergence-free projection on each $v_k$
   until algorithm converges or maximum number iterations reached

---

In certain embodiments, the organ deformation motion is modeled using multiple graphics processing units (GPU) in communication with a computer memory storing the anatomical images. Since current computer graphics hardware may include hundreds of separate graphics channels or pipeline, each of these channels can be used in parallel in order to process and reconstruct the anatomical images being used.

In order to provide a more complete explanation of the exemplary method and system described in detail above, an example of applying the described technology will now be provided. While specific imaging machines, processing orders, data, and disease diagnosis will be described, the described systems and methods can use a wide variety of imaging machines and raw data. In addition, it should be appreciated that the methods herein can be used in analyzing any portion of the human anatomy and in diagnosing a large variety of disorders or diseases in the human body.

The following example embodiment was performed using the CIRS anthropomorphic thorax phantom (CIRS Inc., Norfolk, Va.) and a GE Lightspeed RT scanner (GE Health Care, Waukesha, Wis.). The phantom includes a simulated chest cavity with a 2 cm spherical object representing a tumor that is capable of moving in three dimensions. A chest marker is also included in the phantom which moves in a pattern synchronized to the tumor and allows simulation of a real patient 4D RCCT scan. The scans used in this study were driven to simulate a breathing trace collected from a real patient.

Figure 4A:
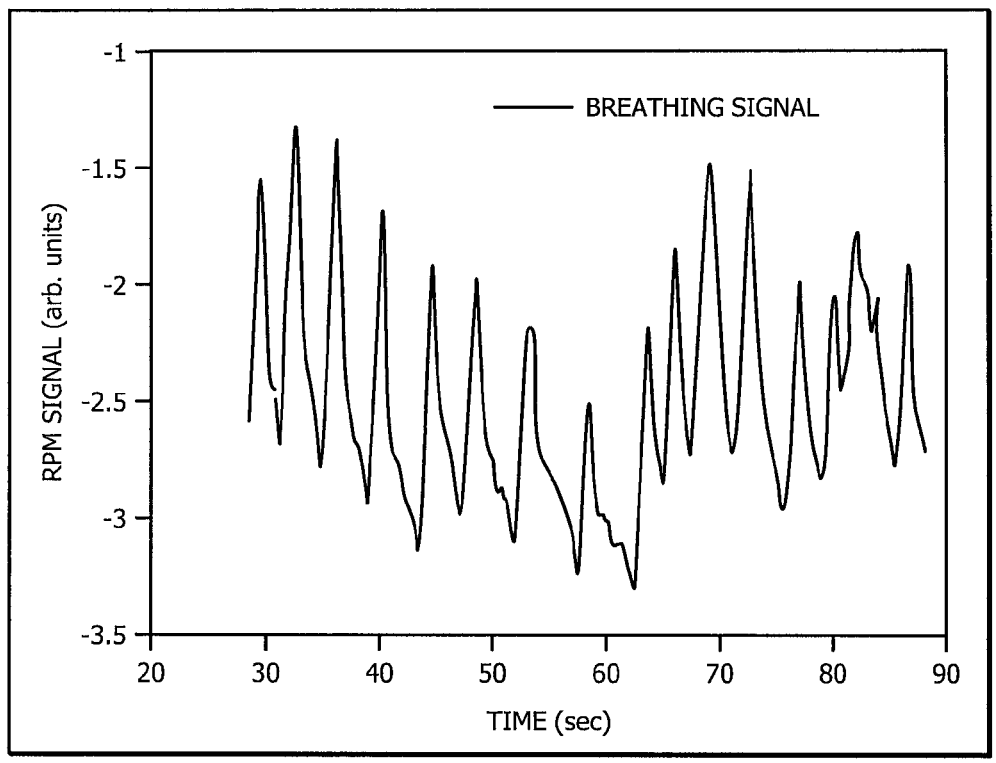
FIG. 4A shows a graph of motion tracking data as utilized in an exemplary embodiment providing image reconstruction with respect to a phantom.
Figure 4B:
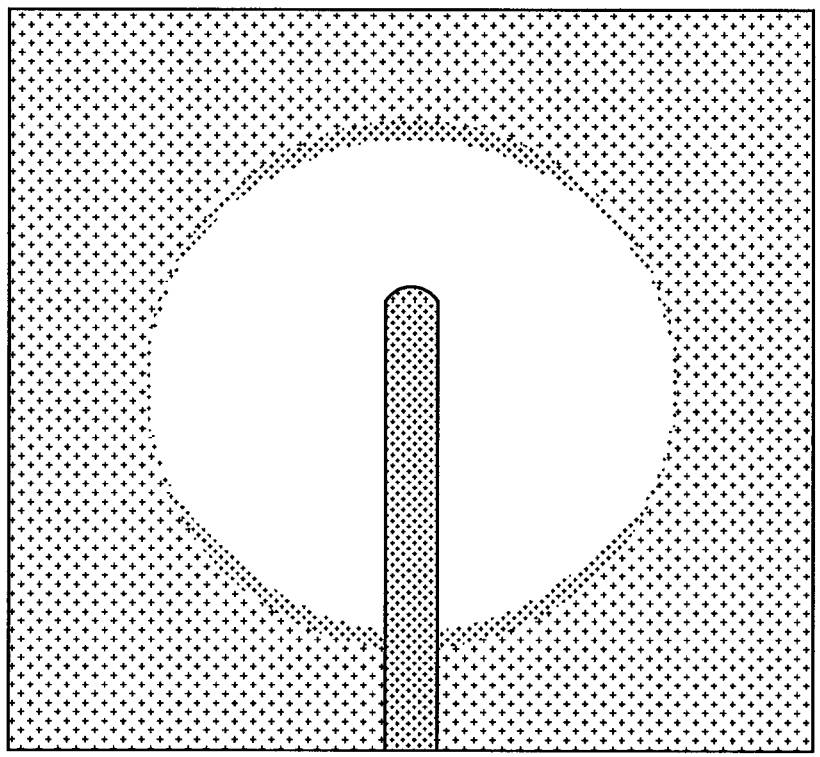
FIG. 4B shows the stationary phantom of the exemplary embodiment of FIG. 4A imaged with helical CT.
Figure 5:
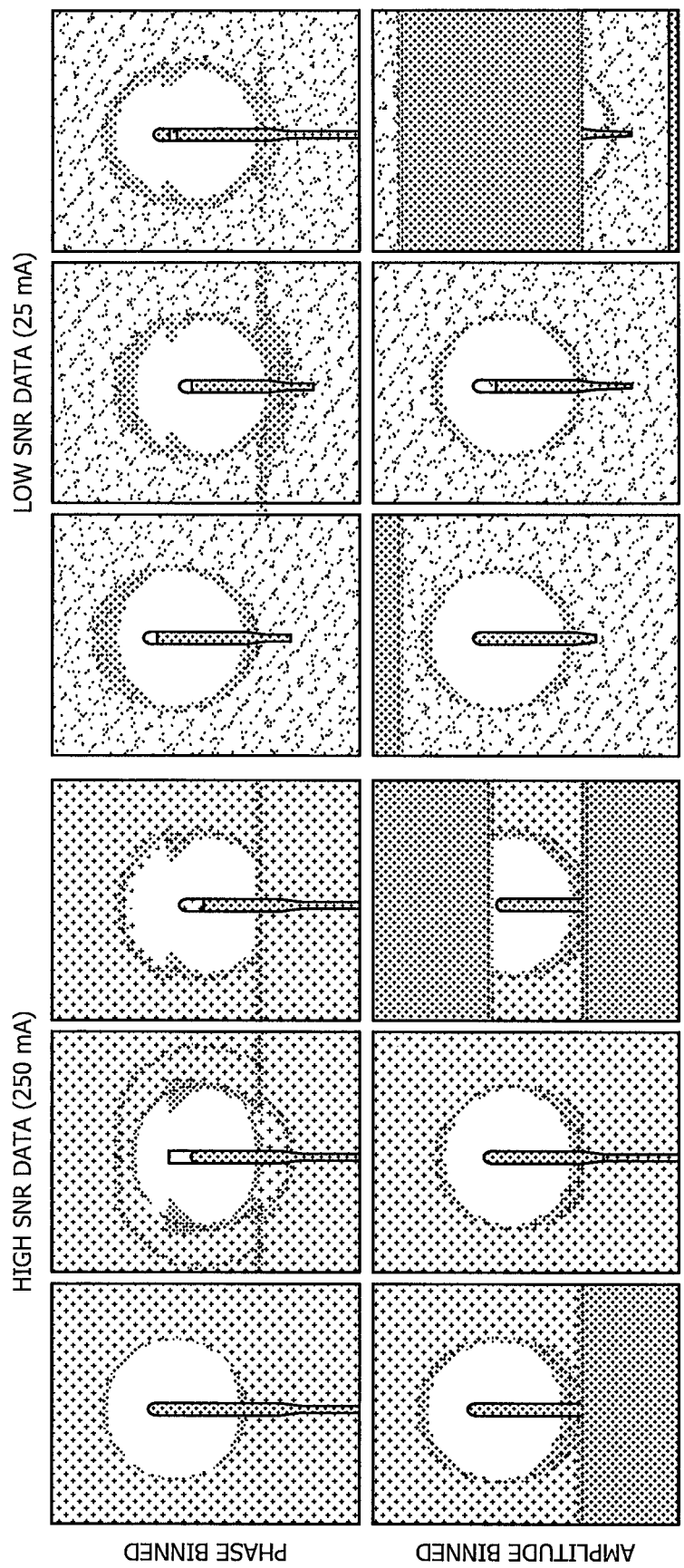
FIG. 5 shows the 4D reconstructed images from a phase binned dataset (top row) and an amplitude binned dataset (bottom row) of the phantom of FIG. 4B.

The recorded RPM trace (motion tracking data) of the aforementioned experimental setup is shown in FIG. 4A while the stationary spherical CIRS lung tumor phantom imaged with helical CT is shown in FIG. 4B. The 4D phase binned dataset of the CIRS phantom generated by the GE Advance Workstation is shown in the top row of FIG. 5. Specifically, the top row of FIG. 5 shows phase binned images at three different phases for the high SNR data (left) and the low SNR (10% tube current) data (right). Binning artifacts, including mismatched slices in the phase binned data when compared with the image of the stationary phantom, can readily be seen in the reconstructed phase binned images of FIG. 5. Shown in the bottom row of FIG. 5 are images from an amplitude binned dataset at peak-inhale, mid-range amplitude, and peak-exhale for both the high and low SNR data. The reconstructed images from the amplitude binned dataset do not show signs of mismatched slices and more closely resemble the static phantom image but suffer from missing data artifacts.

Figure 6A:
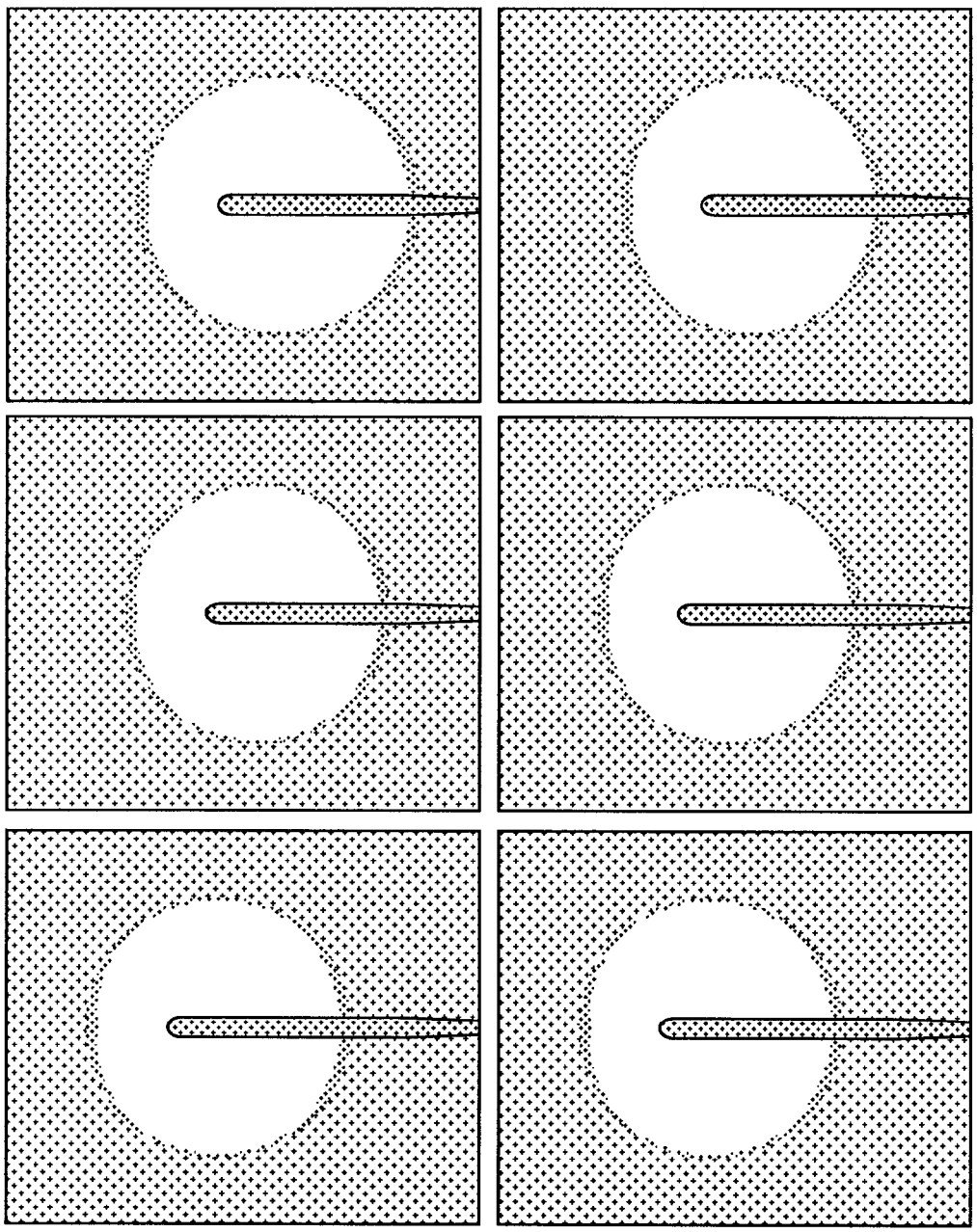
FIG. 6A shows the 4D reconstructed images generated according to the concepts herein using the same raw data as the phase and amplitude binned images in FIG. 5.
Figure 6B:
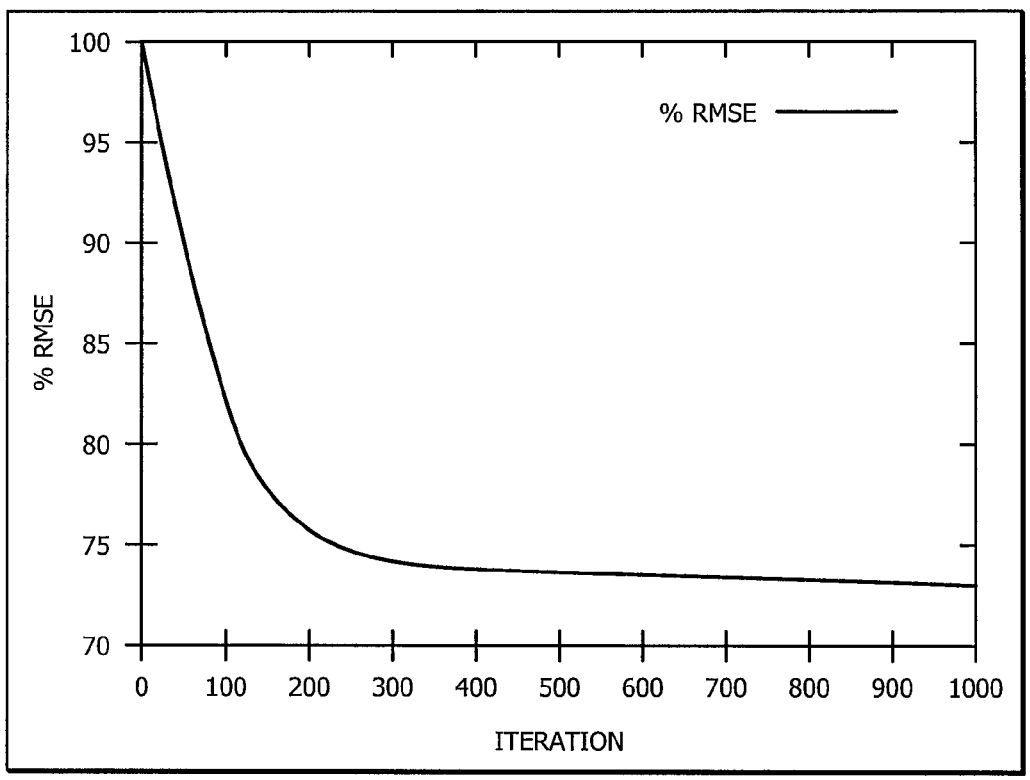
FIGS. 6B and 6C show plots of the posterior indicating the convergence of the embodiment of the concept as applied in FIG. 6A.
Figure 6C:
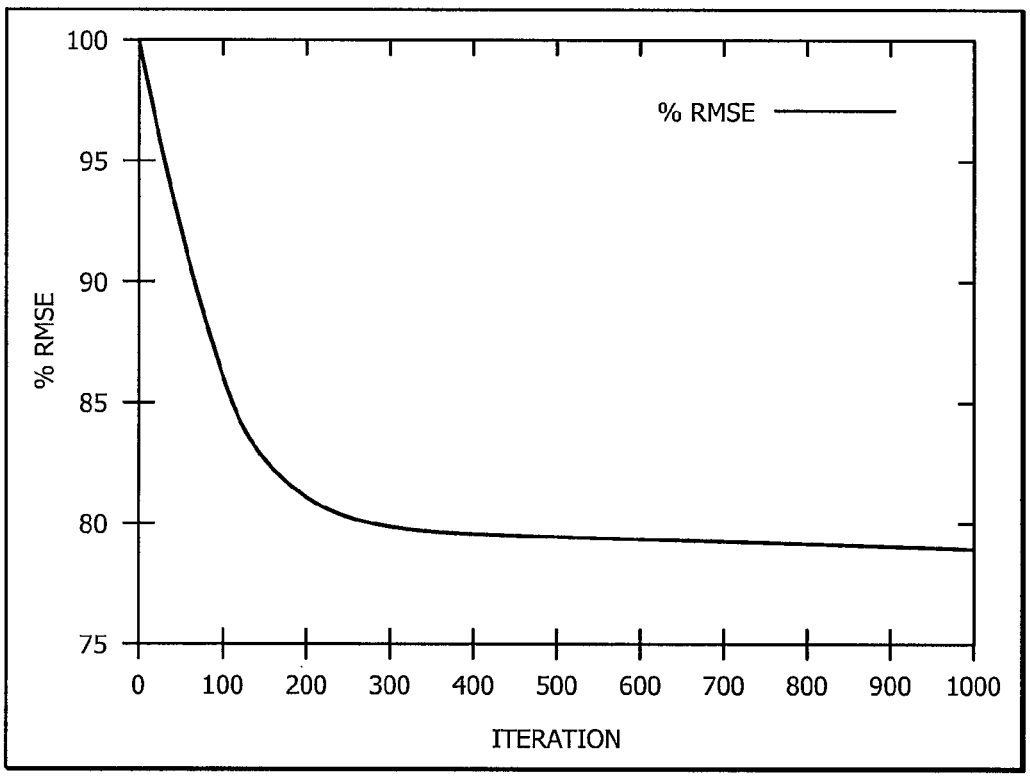

Because access to the raw projection data was not available in performing the experimentation of this example (i.e., the raw image projection data was not available from the GE Lightspeed RT scanner), the slow motion assumption described above was applied when using the CINE slice data along with the recorded RPM trace in the 4D reconstruction algorithm. In order to demonstrate robustness against noise, an initial scan was taken with an X-ray tube current of 250 mA then repeated with a tube current of 25 mA. FIG. 6A shows the 4D reconstructed images generated according to the concepts herein using the same raw data as the phase and amplitude binned images in FIG. 5. Specifically, FIG. 6A shows 4D reconstructed images of the phantom at end-inhale, mid-range, and end-exhale amplitudes. The top row shows the 4D reconstruction of the high SNR data, while the bottom row shows that of the low SNR data. It should be appreciated that the reconstructed image as shown in FIG. 6A does not have any artifacts associated with either the phase binning or amplitude binning. Moreover, an increase in SNR in the 4D reconstructed images. For example, reconstructed 4D images from 25 mA data have higher signal-to-noise ratio (SNR=76.5) than binned images reconstructed using 250 mA data (SNR=53.9). The similarity in images between the two 4D reconstructions shows the robustness of the image estimation to increasing noise. FIGS. 6B and 6C show plots of the posterior indicating the convergence of the method.

Figure 7A:
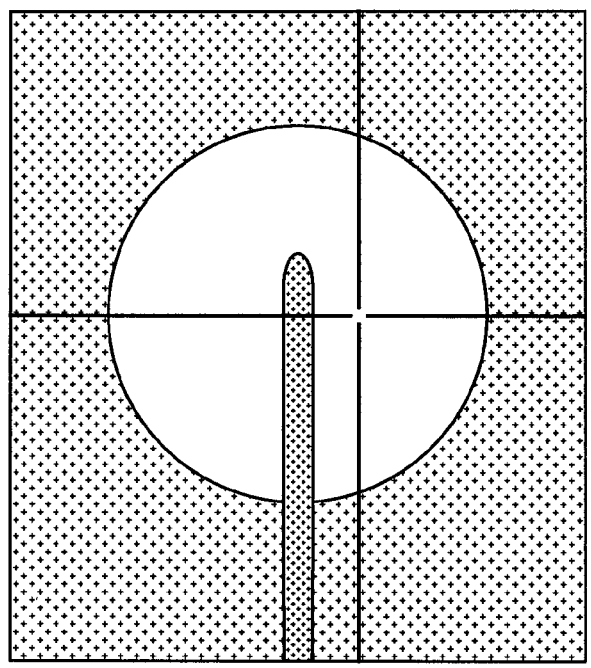
FIG. 7A shows a single point in the phantom of FIG. 4B tracked for analyzing displacement versus motion tracking data as shown in FIGS. 7B and 7C.
Figure 7B:
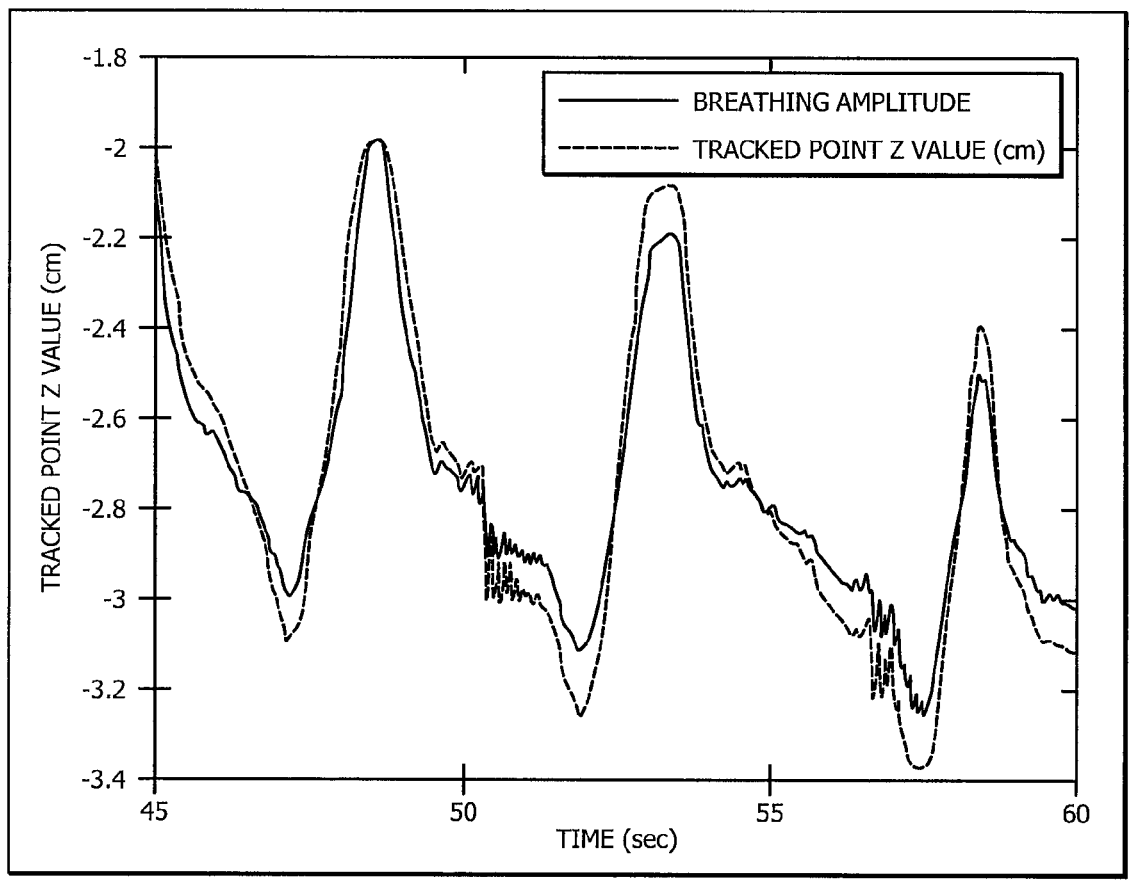
FIG. 7B shows a graph of motion tracking data as utilized in the analysis of FIG. 7C.
Figure 7C:
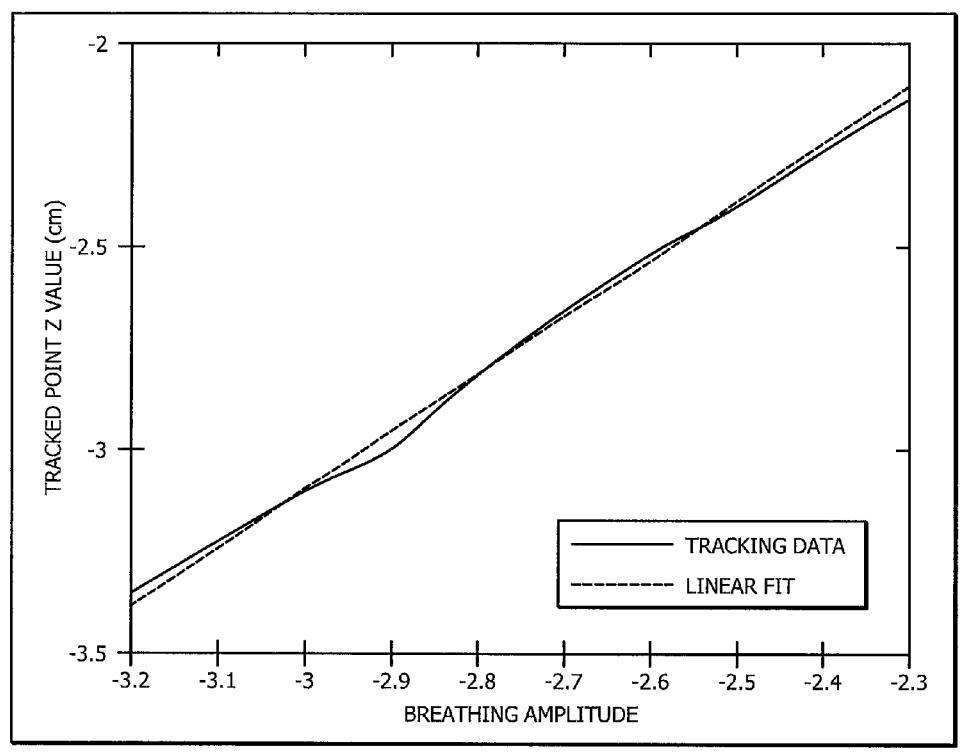
FIG. 7C shows a plot of the estimated displacements versus the motion tracking data of FIG. 7B for the point indicated in FIG. 7A.

To validate the estimated deformation model, a single point at the center of the phantom indicated by the cross hair in FIG. 7A was tracked by integrating the estimated velocity fields according to equation 4. The physical construction of the phantom dictates that the superiorinferior displacement is linearly correlated to the RPM signal. Shown in FIG. 7C is a plot of the estimated displacements versus the RPM signal (motion tracking data) of FIG. 7B. As can readily be appreciated from the graph of FIG. 7C, there is an excellent linear correlation (r=0.9988) between the estimated displacements and the RPM signal, thus validating the deformation estimation process.

Figure 8:
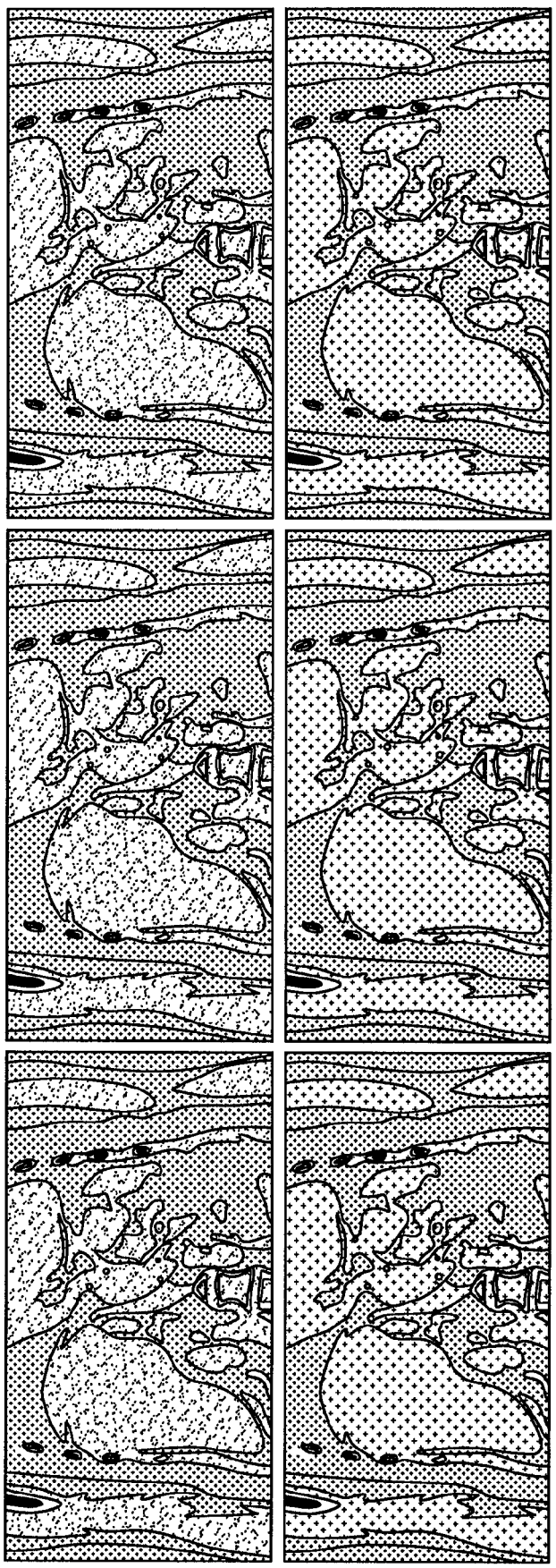
FIG. 8 shows a comparison between phase binning reconstructed images (top row) and the 4D reconstructed images according to the concepts herein (bottom row) at peak-exhale, mid-range, and peak-inhale.

Having described an example of applying the described technology using the CIRS anthropomorphic thorax phantom, an example of applying the described technology to a real patient is described below to further facilitate an understanding of the concepts herein. Specifically, a 4D reconstruction method as described herein was also applied to data collected from a real patient undergoing hypo-fractionated radiation therapy treatment of the liver. FIG. 8 provides a comparison between phase binning reconstructed images (top row) and the 4D reconstructed images according to the concepts herein (bottom row) at peak-exhale, mid-range, and peak-inhale. In addition to improving SNR, slice mismatch artifacts are absent in the 4D reconstructed image as is readily apparent in FIG. 8.

Figure 9:
FIG. 9 shows 4D reconstructed images (top row) and log Jacobian determinant images (bottom row) for compressible flow reconstruction (left column) and with incompressibility constraint (right column).

In this exemplary embodiment, the 4D reconstruction algorithm was run with and without the incompressibility constraint. Analysis of the incompressibility projection is shown in FIG. 9. Specifically, FIG. 9 shows 4D reconstructed images (top row) and log Jacobian determinant images (bottom row) for compressible flow reconstruction (left column) and with incompressibility constraint (right column). Negative log Jacobian values indicate local compression, while positive values indicate expansion. The reconstructed images are extremely similar, while the Jacobian maps (bottom row) are quite different. In particular, it is seen that without the incompressibility constraint, the estimated motion indicates compression and expansion of the top and bottom of the liver, while the incompressible reconstruction shows no local expansion or contraction. This illustrates the fact that although the two methods produce very similar images, the motion estimates are quite different. Given that liver is a blood-filled organ, physiologically it does not undergo any appreciable local changes in volume due to breathing. This exemplifies the usefulness of incorporating incompressibility into the reconstruction process.

While exemplary embodiments of the present technology have been described in terms of using certain types of medical scanners, the technology can be used with any type of medical scanner that is currently available or which may be become available that can provide images of a patients external or internal anatomy. Examples of medical imaging scanners that can be used with the present technology include but are not limited to: PET (Positron Emission Tomography) scanning, CT (computed tomography) scanning, combined PET/CT scanning, MRI (Magnetic Resonance Imaging) scanning, radio frequency (RF) scanning, millimeter wave scanning, holographic scanning, conebeam scanners, other nuclear medicine oriented types of scanning devices, and/or the like. The following discussion provides detail with respect to application of the concepts herein to several of the foregoing variations of medical scanners.

In providing 4D conebeam image reconstruction according to an embodiment of the invention, start with the log posterior $$L(I_0 \upsilon \mid p_i) = -\|\upsilon(a)\|_V^2 - \frac{1}{2\sigma^2} \sum_i \int_S |P_{\theta_i}\{I_0 \circ h(a_i, \cdot)\}(s) - p_i(s)|^2 \, ds, \quad (20)$$

with or without the constraint div $\upsilon=0$. Note now that $s \in R^2$ and the projection operator is a conebeam projection.

A first variation of equation 20 with respect to $\upsilon_k$ is given by $$\delta_{\upsilon_k} L(I_0, \upsilon_k \mid p_i) = -2v_k - \quad (21)$$
$$\frac{1}{\sigma^2}(L^\dagger L)^{-1} \sum_i P_{\theta_i}^\dagger (P_{\theta_i}\{I_0 \circ h(a_i, \cdot)\} - p_i) \circ h_{a_i}^{-1}(a_k, \cdot) b_i(k, \cdot),$$

where $$b_i(k, \vec{x}) = \begin{cases} 0 & a_i \le a_k \\ \frac{a_i - a_k}{\Delta a} \nabla I_k\left(\vec{x} + \frac{a_i - a_k}{\Delta a} \upsilon_k(\vec{x})\right) & a_k < a_i \le a_{k+1} \\ |D(h_{a_{k+1}} \circ h_{a_i}^{-1})(\vec{x})| \nabla I_k(\vec{x} + \upsilon_k(\vec{x})) & a_i > a_{k+1}. \end{cases} \quad (22)$$

A first variation of equation 20 with respect to $I_0$ is $$\delta_{I_0} L(I_0, \upsilon \mid p_i) = \quad (23)$$
$$\frac{1}{\sigma^2} \sum_i |Dh^{-1}(a_i, \cdot)| \left( P_{\theta_i}^\dagger P_{\theta_i}\{I_0 \circ h(a_i, \cdot)\} - P_{\theta_i}^\dagger p_i \right) \circ h^{-1}(a_i, \cdot).$$

Notice that the image variation is computed by computing the $(P_{\theta_i}^\dagger P_{\theta_i}\{I_0 \bigcirc h(a_i, \cdot)\} - P_{\theta_i}^\dagger p_i)$ difference images then splatting them back to a=0 and summing. The difference image calculation is expensive and should be done for every projection. Note also that the velocity variations are computed by computing all difference images, and adding it (splatted) to all past velocity field body forces, then applying the Green's function to the summed body force.

The foregoing means both variations can be computed efficiently simultaneously. For each projection $p_i$, the image is pushed forward to amplitude $a_i$ (cascaded interpolation). Then the difference image is obtained (CUDA projection/adjoint operation). This difference image is then pulled back to each amplitude discretization (splatting), where it is multiplied by the image gradient and added to the body force for that velocity field gradient. Finally, when it is pulled back to the base amplitude it is also added to the image gradient.

In deriving a formula for $P_\theta\{I\}(u,v)$, assume that the source/detector rotate in a circular (as opposed to helical/spiral) trajectory about the center of the volume and that the X-ray source is located a distance $d_x$ from the center of rotation while the detector plane is a distance $d_p$. The projection angle $\theta$ is defined as the angle between the source position and the positive x axis.

It is important to recognize that helical conebeam simply amounts to shifting the input image before projection, according to the z value at which the projection was obtained. It should be appreciated that fanbeam CT acquisition is identical to conebeam acquisition except that the detector image has only one row of detectors at u=0. Thus, helical fanbeam CT can likewise be implemented by shifting the input. The method introduced here, therefore, encompasses variations of fanbeam or conebeam CT acquisition.

Assume the center of rotation is $0 \in \mathbb{R}^3$ and that the detector rotates in the xy plane only. The source position depends on $\theta$, call it $s_\theta = (d_x \cos\theta, d_x \sin\theta, 0) \in \mathbb{R}^3$. The position (index) in the projection image is denoted by $(u,v) \in \mathbb{R}^2$, with the point $(u,v)=0$ collinear with both $s_\theta$ and 0.

The projection image has value at each position equal to the integral of the image from the source position to the detector position. The detector position can be determined in world coordinates from $(u,v)$ via $$\omega_\theta(u,v) = \begin{pmatrix} -d_p\cos\theta - u\sin\theta \\ -d_p\sin\theta + u\cos\theta \\ v \end{pmatrix}$$

Now the projection is given by $$P_\theta\{I\}(u,v) = \int_{l_{min}}^{l_{max}} \cos^3\gamma(u,v) I\left(s_\theta + l\frac{\omega_\theta(u,v) - s_\theta}{\|\omega_\theta(u,v) - s_\theta\|}\right) dl, \quad (24)$$

where $l_{min}, l_{max}$ are the minimum and maximum distances of the image domain to the source as it rotates and $\gamma(u,v)$ is the angle between the line from the source to the plane's midpoint and the ray from source to the point $(u,v)$. The cosine term comes from the $1/r^2$ falloff of the radiation and from the tilting of the detector elements. Note that cos $\gamma$ takes the convenient form $$\cos\gamma(u,v) = \frac{d}{\sqrt{u^2 + v^2 + d^2}}$$

For simplicity the transformation $r: R2 \times [l_{min}, l_{max}] \to R^3$ is introduced, which is given by $$r_\theta(u,v,l) = s_\theta + l\frac{\omega_\theta(u,v) - s_\theta}{\|\omega_\theta(u,v) - s_\theta\|} \quad (25)$$

$$= \begin{pmatrix} d_x\cos\theta \\ d_x\sin\theta \\ 0 \end{pmatrix} + \frac{l}{\sqrt{u^2 + v^2 + d^2}} \begin{pmatrix} -d\cos\theta - u\sin\theta \\ -d\sin\theta + u\cos\theta \\ v \end{pmatrix}$$

Now the projection has the simple form $$P_\theta\{I\}(u,v) = \int_{l_{min}}^{l_{max}} \frac{d^3}{(u^2 + v^2 + d^2)^{3/2}} I \circ r_\theta(u,v,l) dl. \quad (26)$$

For backprojection a formula for $P_\theta^\dagger\{p\}(x,y,z)$ may be derived. Note that in order to not accumulate stuff that never gets projected, the backprojection should be limited to be zero in areas that are never integrated. At each point $(x,y,z) \in \Omega$, the furthest source position may be found and checked if it is within $l_{max}$ of the point. This may be performed by checking if $(d_x + \sqrt{x^2+y^2})^2 + z^2 < l_{max}^2$.

The Jacobian of the transformation $r_\theta(u,v,l)$ should be found. The derivatives are $$\frac{\partial r_{\theta,x}}{\partial u} = -l\sin\theta \frac{v^2 + d^2}{(u^2 + v^2 + d^2)^{3/2}} \quad (27)$$

$$\frac{\partial r_{\theta,y}}{\partial u} = l\cos\theta \frac{v^2 + d^2}{(u^2 + v^2 + d^2)^{3/2}} \quad (28)$$

$$\frac{\partial r_{\theta,z}}{\partial u} = -luv \frac{1}{(u^2 + v^2 + d^2)^{3/2}} \quad (29)$$

$$\frac{\partial r_{\theta,x}}{\partial v} = luv\sin\theta \frac{1}{(u^2 + v^2 + d^2)^{3/2}} \quad (30)$$

$$\frac{\partial r_{\theta,y}}{\partial v} = -luv\cos\theta \frac{1}{(u^2 + v^2 + d^2)^{3/2}} \quad (31)$$

$$\frac{\partial r_{\theta,z}}{\partial v} = l\frac{u^2 + d^2}{(u^2 + v^2 + d^2)^{3/2}} \quad (32)$$

$$\frac{\partial r_{\theta,x}}{\partial l} = (-d\cos\theta - u\sin\theta)\frac{u^2 + v^2 + d^2}{(u^2 + v^2 + d^2)^{3/2}} \quad (33)$$

$$\frac{\partial r_{\theta,y}}{\partial l} = (-d\sin\theta + u\cos\theta)\frac{u^2 + v^2 + d^2}{(u^2 + v^2 + d^2)^{3/2}} \quad (34)$$

$$\frac{\partial r_{\theta,z}}{\partial l} = v\frac{u^2 + v^2 + d^2}{(u^2 + v^2 + d^2)^{3/2}} \quad (35)$$

Putting these together, the Jacobi matrix is given $$Dr(u,v,l) = \frac{1}{(u^2 + v^2 + d^2)^{3/2}} \quad (36)$$

$$\begin{pmatrix} -l\sin\theta(v^2 + d^2) & l\cos\theta(v^2 + d^2) & -luv \\ luv\sin\theta & -luv\cos\theta & l(u^2 + d^2) \\ (-d\cos\theta - u\sin\theta) & \frac{(-d\sin\theta + u\cos\theta)}{(u^2 + v^2 + d^2)} & v(u^2 + v^2 + d^2) \end{pmatrix}$$

Taking the determinant it can bee seen that $$\det Dr(u,v,l) = \frac{-l^2 d^3}{(u^2 + v^2 + d^2)^{5/2}} \quad (37)$$

Since an expression for $P_\theta\{I\}(u,v)$ is available, the adjoint may be found by rearranging:

$$\langle P_\theta^\dagger\{p\}, I\rangle_{L^2(R^3)} = \langle p, P_\theta\{I\}\rangle_{L^2(R^2)} \quad (38)$$

$$= \int\int_u \int_v p(u,v) \int_{l_{min}}^{l_{max}} \frac{d^3}{(u^2+v^2+d^2)^{3/2}} \quad (39)$$
$$I \circ r_\theta(u,v,l) dl du dv$$

$$= \int\int_u \int_v \int_{l_{min}}^{l_{max}} p(u,v) \frac{d^3}{(u^2+v^2+d^2)^{3/2}} \quad (40)$$
$$I \circ r_\theta(u,v,l) \frac{|\det Dr_\theta(u,v,l)|}{|\det Dr_\theta(u,v,l)|} dl du dv$$

$$= \int_x \frac{p(u(x), v(x))}{|\det Dr_\theta(u(x), v(x), l(x))|} \quad (41)$$
$$\frac{d^3}{(u(x)^2+v(x)^2+d^2)^{3/2}} I(x) dx$$

$$= \int_x p(u(x), v(x)) \frac{u(x)^2+v(x)^2+d^2}{l(x)^2} I(x) dx. \quad (42)$$

The foregoing uses $u(x), v(x), l(x)$ to denote the components of $r_\theta^{-1}(x)$.

For static gradient descent with optimal step size the noise may be modeled as Gaussian. Thus, the following is to be minimized $$J(I) = \sum_i \int\int_u \int_v [P_\theta\{I\}(u,v) - p_i(u,v)]^2 du dv \quad (43)$$

with respect to the image $I \in L^2(R^3)$.

Supposing a current image estimate $I^k$ and $I^{k+1}$ is to be computed, a first variation of $J$ with respect to $I$ at $I^k$ is $$\delta_I J(I^k) = 2\sum_i P_{\theta_i}^\dagger \{P_{\theta_i}\{I^k\} - p_i\}$$

Now the updated image is simply $I^{k+1} = I^k - \alpha \delta_I J(I^K)$, where alpha is some step size. It is preferred that the optimal a be chosen. To do this consider the updated cost function.

$$J(I^{k+1}) = \sum_i \int\int_u \int_v [P_{\theta_i}\{I^k - \alpha\delta_I J(I^k)\}(u,v) - p_i(u,v)]^2 du dv \quad (44)$$

The derivative of this with respect to $\alpha$ is taken in order to optimize:

$$\frac{\partial J(I^{k+1})}{\partial \alpha} = \sum_i \int\int_u \int_v 2[P_{\theta_i}\{I^k - \alpha\delta_I J(I^k)\}(u,v) - p_i(u,v)] \quad (45)$$
$$P_{\theta_i}\{\delta_I J(I^k)\}(u,v) du dv.$$

$$= 2\sum_i \left\langle \begin{array}{c} P_{\theta_i}\{I^k\} - \alpha P_{\theta_i}\{\delta_I J(I^k)\} - \\ p_i, P_{\theta_i}\{\delta_I J(I^k)\} \end{array} \right\rangle_{L^2(R^2)} \quad (46)$$

$$= 2\sum_i \langle P_{\theta_i}\{I^k\} - p_i, P_{\theta_i}\{\delta_I J(I^k)\}\rangle_{L^2(R^2)} - \quad (47)$$
$$\alpha\langle P_{\theta_i}\{\delta_I J(I^k)\}, P_{\theta_i}\{\delta_I J(I^k)\}\rangle_{L^2(R^2)}.$$

$$= 2\left\langle \sum_i P_{\theta_i}^\dagger (P_{\theta_i}\{I^k\} - p_i), \delta_I J(I^k)\right\rangle_{L^2(R^2)} - \quad (48)$$
$$2\alpha\left\langle \sum_i P_{\theta_i}^\dagger P_{\theta_i}\{\delta_I J(I^k)\}, \delta_I J(I^k)\right\rangle_{L^2(R^2)}$$

$$= 2\langle \delta_I J(I^k), \delta_I J(I^k)\rangle_{L^2(R^2)} - \quad (49)$$
$$2\alpha\left\langle \sum_i P_{\theta_i}^\dagger P_{\theta_i}\{\delta_I J(I^k)\}, \delta_I J(I^k)\right\rangle_{L^2(R^2)}$$

Clearly this is zero when $$\alpha = \frac{\|\delta_I J(I^k)\|^2_{L^2(R^2)}}{\left\langle \sum_i P_{\theta_i}^\dagger P_{\theta_i}\{\delta_I J(I^k)\}, \delta_I J(I^k)\right\rangle_{L^2(R^2)}} \quad (50)$$

A 4D reconstruction method for conebeam data according to embodiments of the present invention is set forth in the pseudocode below. It should be appreciated that "streakdiff" is used in the below pseudocode for the velocities and the image update. This is where the optimization (and GPU) come in.

| Pseudocode for 4D reconstruction of conebeam data |
| --- |
| $I_0 \leftarrow$ Feldkamp $(\{p_i\}_i)$<br>for each k do<br>  $v_k \leftarrow 0$<br>end of<br>repeat<br>  for each projection i do<br>    Compute streakdiff[i] = $P_{\theta i}^\dagger (P_{\theta i} \{I_0 \circ h(a_i, \cdot)\} - p_i)$<br>  end for<br>  for each time step k do<br>    $v_k \leftarrow v_k + \epsilon \delta_{v_k} L(I_0, v_k)$<br>  end of<br>  $I_0 \leftarrow I_0 - \delta_{I_0} L(I_0, v)$<br>  Perform divergence-free projection on each $v_k$<br>until algorithm converges or maximum number iterations reached |

As another example, in providing 4D MRI image reconstruction according to an embodiment of the invention, start with Start with the log posterior $$L(I_0 v \mid p_i) = -\|v(a)\|_V^2 - \frac{1}{2\sigma^2}\sum_i \int_S |P_{\theta_i}\{I_0 \circ h(a_i, \cdot)\}(s) - p_i(s)|^2 ds, \quad (51)$$

with or without the constraint div $v=0$. Note now that $\in \Omega_d$ is a point in the data domain, which is some subspace of $R^3$. If enough temporal resolution exists each sample point in k-space can be treated as an individual projection. This may not be practical since the time between samples in the readout direction is typically a few milliseconds. More commonly, $\Omega_d$ is a line or plane in $R^3$. The case of lines will be considered in the following example. However, it should be appreciated that planar k-space data may be implemented easily as simply a collection of lines.

A first variation of equation 51 with respect to $v_k$ is given by $$\delta_{v_k} L(I_0, v_k | p_i) = -2v_k - \frac{1}{\sigma^2}(L^\dagger L)^{-1} \sum_i P_{\theta_i}^\dagger (P_{\theta_i}\{I_0 \circ h(a_i, \cdot)\} - p_i) \circ h_{a_i}^{-1}(a_k, \cdot) b_i(k, \cdot), \quad (52)$$

where $$b_i(k, \vec{x}) = \begin{cases} 0 & a_i \leq a_k \\ \frac{a_i - a_k}{\Delta a} \nabla I_k\left(\vec{x} + \frac{a_i - a_k}{\Delta a} v_k(\vec{x})\right) & a_k < a_i \leq a_{k+1} \\ |D(h_{a_{k+1}} \circ h_{a_i}^{-1})(\vec{x})|\nabla I_k(\vec{x} + v_k(\vec{x})) & a_i > a_{k+1}. \end{cases} \quad (53)$$

A first variation of equation 51 with respect to $I_0$ is $$\delta_{I_0} L(I_0, v | p_i) = \quad (54)$$

$$\frac{1}{\sigma^2} \sum_i |Dh^{-1}(a_i, \cdot)|\left(P_{\theta_i}^\dagger P_{\theta_i}\{I_0 \circ h(a_i, \cdot)\} - P_{\theta_i}^\dagger p_i\right) \circ h^{-1}(a_i, \cdot).$$

Notice that the image variation is computed by computing the $(P_{\theta_i}^\dagger P_{\theta_i}\{I_0 \bigcirc h(a_i, \cdot)\} - P_{\theta_i}^\dagger p_i)$ difference images then splatting them back to a=0 and summing. The difference image calculation is expensive and should be done for every projection. Note also that the velocity variations are computed by computing all difference images, and adding it (splatted) to all past velocity field body forces, then applying the Green's function to the summed body force.

The foregoing means both variations can be computed efficiently simultaneously. For each projection $p_i$, the image is pushed forward to amplitude $a_i$ (cascaded interpolation). Then the difference image is obtained (CUDA projection/adjoint operation). This difference image is then pulled back to each amplitude discretization (splatting), where it is multiplied by the image gradient and added to the body force for that velocity field gradient. Finally, when it is pulled back to the base amplitude it is also added to the image gradient.

In deriving a formula $P_i\{I\}$ (s), assume $s \in \Omega_d$ and $\Omega_d$ some set of points in $R^3$. Further assume it is a line in the x direction, as this is generally the readout direction for a standard gradient echo scan. The position of the line in the Fourier domain is given by $v_i$, $w_i$. In MRI the Fourier transform of the anatomy is measured directly, so that the projection operator takes a very simple form.

$$P_i\{I\}(u) = F_{3D}\{I\}(u, v_i, \omega_i). \quad (55)$$

Explicitly this is $$P_i\{I\}(u) = \int_x \int_y \int_z I(x,y,z) e^{-2\pi i(ux+v_i y+\omega_i z)} dx dy dz \quad (56)$$

For backprojection, in the case that $\Omega_d$ is a line as we described previously, the inner product in $L^2(R)$ may be used to derive the adjoint operator.

$$\langle I, P_i^\dagger\{p\}\rangle_{L^2(R^3)} = \langle P_i\{I\}, p\rangle_{L^2(R)} \quad (57)$$

$$= \int_u P_i\{I\}^* \varphi(u) du \quad (58)$$

$$= \int_u \int_x \int_y \int_z I(x, y, z) * e^{2\pi i(ux+v_i y+\omega_i z)} dx dy dz \varphi(u) du \quad (59)$$

$$= \int_x \int_y \int_z I(x, y, z) * \int_u e^{2\pi i(ux+v_i y+\omega_i z)} \varphi(u) du dx dy dz \quad (60)$$

$$= \left\langle I, \int_u e^{2\pi i(ux+v_i y+\omega_i z)} \varphi(u) du \right\rangle_{L^2(R^3)}. \quad (61)$$

The formula for the adjoint operator may thus be seen as $$P_i^\dagger\{p\}(x, y, z) = \int_u e^{2\pi i(ux+v_i y+\omega_i z)} \varphi(u) du \quad (62)$$

$$= e^{2\pi i(v_i y+\omega_i z)} F_u^{-1}\{\varphi(u)\}(x) \quad (63)$$

A 4D reconstruction method for MRI data according to embodiments of the present invention is set forth in the pseudocode below. "Streakdiff" is again used in the below pseudocode for the velocities and the image update.

| Pseudocode for 4D reconstruction of MRI data |
|---|
| $I_0 \leftarrow$ Feldkamp $(\{p_i\}_i)$ |
| for each k do |
|     $v_k \leftarrow 0$ |
| end of |
| repeat |
|     for each projection i do |
|         Compute streadkdiff[i] = $P_{\theta i}^\dagger$ ($P_{\theta i}$ $\{I_0 \circ h(a_i, \cdot)\}$− $p_i$) |
|     end for |
|     for each time step k do |
|         $v_k \leftarrow v_k + \epsilon \delta_{v_k} L(I_0, v_k)$ |
|     end of |
|     $I_0 \leftarrow I_0 - \delta_{I_0} L(I_0, v)$ |
|     Perform divergence-free projection on each $v_k$ |
| until algorithm converges or maximum number iterations reached |

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising:
   collecting raw image data for a subject being imaged, wherein the subject being imaged comprises at least one structure;
   obtaining motion tracking data associated with the subject being imaged;
   receiving estimated complex deformation motion parameters relevant to the at least one structure;
   reconstructing an estimated image of the subject being imaged from the raw image data by modeling structure deformation motion of the at least one structure using the motion tracking data and the received complex deformation motion parameters; and
   indexing the obtained motion tracking data with the collected raw image data,
   wherein said reconstructing an estimated image includes utilizing the indexed data and complex deformation parameters to provide a 4D image reconstruction.

2. The method of claim 1, wherein the raw image data is provided as raw projection data from an imaging modality.

3. The method of claim 2, wherein the imaging modality comprises an imaging modality selected from the group consisting of: a positron emission tomography (PET) imaging modality; a computed tomography (CT) imaging modality; a combined PET/CT imaging modality; a magnetic resonance imaging (MRI) imaging modality; an ultrasound imaging modality; a radio frequency (RF) imaging modality; a millimeter wave imaging modality; a holographic imaging modality; and a nuclear medicine imaging modality.

4. The method of claim 1, wherein the complex deformation motion parameters comprise constraints on possible deformations of the at least one structure.

5. The method of claim 4, wherein the complex deformation motion parameters comprise boundaries regarding at least one of velocity and a change in velocity for the at least one structure.

6. The method of claim 1, wherein the reconstructing an estimated image comprises:
   implementing a maximum a posteriori (MAP) technique using the raw image data to reconstruct images and estimate structure deformations simultaneously.

7. The method of claim 1, wherein the reconstructing an estimated image comprises:
   implementing an alternating optimization algorithm to optimize the modeling structure deformation and to optimize the estimated image.

8. The method of claim 1, wherein the subject being imaged comprises a patient, the at least one structure comprises an anatomical structure of the patient, and the motion tracking data is associated with movement of the anatomical structure during a time in which the raw image data is collected.

9. The method of claim 1, wherein the estimating complex deformation motion parameters comprises structure motion parameters estimated using mathematical analysis techniques selected from the group consisting of: b-spline; polynomial-spline; elastic-spline; ploy-affine; polynomial; and wavelet based.

10. A system comprising:
    a database of structure motion parameters relevant to at least one structure;
    a processor adapted to provide image reconstruction processing resulting in output of an estimated image of a subject being imaged from raw image data by modeling structure deformation motion of the at least one structure using the motion tracking data and structure motion parameters for the at least one structure obtained from the database,
    wherein the obtained motion tracking data is indexed with the collected raw image data, and
    wherein said reconstruction processing resulting in output of an estimated image includes the indexed data and structure motion parameters to provide a 4D image reconstruction.

11. The system of claim 10, further comprising:
    an imaging modality operable to provide the raw image data for the subject being imaged.

12. The system of claim 11, wherein the imaging modality comprises an imaging modality selected from the group consisting of: a positron emission tomography (PET) imaging modality; a computed tomography (CT) imaging modality; a combined PET/CT imaging modality; a magnetic resonance imaging (MRI) imaging modality; an ultrasound imaging modality; a radio frequency (RF) imaging modality; a millimeter wave imaging modality; a holographic imaging modality; and a nuclear medicine imaging modality.

13. The system of claim 10, wherein the database, the processor, and the imaging modality are provided as part of an imaging system.

14. The system of claim 10, further comprising:
    an imaging parameter input providing input of one or more imaging parameters to the processor for use in the image reconstruction processing.

15. The system of claim 14, wherein the one or more imaging parameters include motion tracking data used with the structure motion parameters for modeling structure deformation motion by the processor.

16. The system of claim 10, wherein the structure motion parameters comprise estimated structure motion bounding parameters.

17. A method for reconstructing anatomical images of a patient being medically imaged, the method comprising:
    collecting raw image data from a medical imaging device configured to obtain anatomical images of a patient's internal anatomy;
    receiving a motion tracking signal, wherein the motion tracking signal is related to organ motion as the anatomical images are obtained;
    receiving characteristic complex deformation parameters from a nature of motion database relating to an organ being imaged;
    modeling organ deformation motion for the organ being imaged using the motion tracking signal and the received characteristic complex deformation parameters;
    reconstructing an estimated 4D image of the patient's internal anatomy using the modeled organ deformation motion; and
    indexing the collected raw image data with the received motion tracking signal.

18. The method of claim 17, wherein the estimated 4D image is displayed for viewing by an end user.

19. The method of claim 17, wherein the organ deformation motion is used to reduce motion artifacts in the anatomical images being reconstructed.

20. The method of claim 17, wherein the organ deformation motion is used to increase a signal-to-noise ratio in the anatomical images being reconstructed.

21. The method of claim 17, wherein the organ deformation motion is used to decrease a dose of image modality energy delivered to the patient.

22. The method of claim 17, wherein modeling the organ deformation motion comprises:
   using the motion tracking signal representing organ motion to model a patient's internal organs; and
   obtaining organ deformations by an estimation of anatomical deformation during image reconstruction.

23. The method of claim 17, further comprising:
   estimating structure motion parameters relevant to one or more organ of the patient's internal anatomy from which the raw image data is collected, wherein modeling the organ deformation motion includes using the structure motion parameters with the motion tracking signal to model organ deformation.

24. The method of claim 23, wherein the structure motion parameters comprise structure motion bounding parameters.

25. The method of claim 23, wherein modeling of the organ deformations further includes enforcing conservation of local tissue volume during organ modeling.

26. The method of claim 23, wherein the deformation motion is modeled using diffeomorphic motion model of organ deformations.

27. The method of claim 23, wherein the deformation motion is modeled using movement velocities of the object motion bounding data.

28. The method of claim 17, wherein the organ deformation motion is modeled using multiple graphics processing units (GPU) in communication with a computer memory storing the anatomical images.

29. The method of claim 17, wherein the motion tracking signal represents breathing motion as measured by a motion sensor with the patient.

30. The method of claim 17, wherein the motion tracking signal is derived from the raw image data acquired from the medical imaging device.

31. The method of claim 17, wherein each iteration of computing the images updates of the estimate of the deformation in a gradient ascent step and then updates the image using the associated Euler-Lagrange equation.

* * * * *